United States Patent [19]

Park et al.

[11] Patent Number: 5,625,107
[45] Date of Patent: Apr. 29, 1997

[54] CATALYST FOR CONVERSION OF METHANE TO ETHYLENE, PREPARATION THEREOF, AND PROCESS FOR MANUFACTURING ETHYLENE USING SAID CATALYST

[75] Inventors: Dae C. Park, Daejon; Pyung K. Ahn, Kwangju, both of Rep. of Korea

[73] Assignee: Korea Research Institute of Chemical Technology, Daejon, Rep. of Korea

[21] Appl. No.: 507,280

[22] PCT Filed: Dec. 30, 1994

[86] PCT No.: PCT/KR94/00186

§ 371 Date: Aug. 30, 1995

§ 102(e) Date: Aug. 30, 1995

[87] PCT Pub. No.: WO95/17962

PCT Pub. Date: Jul. 6, 1995

[30] Foreign Application Priority Data

Dec. 31, 1993 [KR] Rep. of Korea ............... 1993/31984

[51] Int. Cl.⁶ .................. C07C 2/24; B01J 27/18; B01J 27/185; B01J 23/75
[52] U.S. Cl. .............. 585/514; 585/500; 585/943; 585/652; 585/651; 585/513; 502/66; 502/74; 502/161; 502/162; 502/208; 502/164; 502/210; 502/166; 502/213; 502/171
[58] Field of Search ................ 502/208, 210, 502/213, 66, 79, 161, 162, 164, 166, 171; 585/500, 943, 652, 651, 513, 514, 515

[56] References Cited

U.S. PATENT DOCUMENTS

| | | | |
|---|---|---|---|
| 4,255,283 | 3/1981 | Bartek et al. | 252/437 |
| 4,346,020 | 8/1982 | Pretzer et al. | 502/161 X |
| 4,484,002 | 11/1984 | Lin | 502/161 X |
| 4,567,307 | 1/1986 | Jones et al. | 585/500 X |
| 4,665,259 | 5/1987 | Brazdil et al. | 585/500 |
| 4,895,987 | 1/1990 | Duggan et al. | 568/648 |
| 5,066,629 | 11/1991 | Lukey et al. | 502/84 |
| 5,068,485 | 11/1991 | Iton et al. | 585/500 |
| 5,068,486 | 11/1991 | Han et al. | 585/500 |
| 5,118,654 | 6/1992 | Choudhary et al. | 585/500 X |

FOREIGN PATENT DOCUMENTS

| | | |
|---|---|---|
| 2016675 | 11/1991 | Canada . |
| 0205117 | 12/1986 | European Pat. Off. . |
| 62-238220 | 10/1987 | Japan . |
| 4-352730 | 12/1992 | Japan . |
| 4-368342 | 12/1992 | Japan . |
| 6-157359 | 6/1994 | Japan . |
| 2253858 | 9/1992 | United Kingdom . |

*Primary Examiner*—Douglas J. McGinty
*Attorney, Agent, or Firm*—Keck, Mahin & Cate

[57] ABSTRACT

The present invention relates to a new catalyst for converting methane into ethane, preparation thereof, and process for manufacturing ethylene using said catalyst. The conversion reaction catalyst in the present invention is employed in converting directly methane or methane-containing gas in the presence of the above catalyst with the following general formula (1).

$$Ma.Pc.D/S \qquad (1)$$

Where,

M is a metal cluster or metal complex compound selected from the group of VIII, VII and VI series;

S is an inorganic carrier;

P is a promoter of phosphorus compound;

D is a cobalt compound.

And "a" is weight percentage of metal cluster or metal complex compound in catalyst, having a value of 0.01 to 10, "c" is weight percentage of promoter in catalyst, ranging from 1.0 to 35.0.

9 Claims, No Drawings

CATALYST FOR CONVERSION OF METHANE TO ETHYLENE, PREPARATION THEREOF, AND PROCESS FOR MANUFACTURING ETHYLENE USING SAID CATALYST

FIELD OF THE INVENTION

The present invention relates to supported catalyst for converting methane into ethylene, preparation thereof, and process for manufacturing ethylene using said catalyst. More particularly, the present invention relates to a new catalyst which is expressed in the following general formula (1) for conversion reaction, preparation thereof, and process for preparation of ethylene by converting directly methane or methane-containing gas in the presence of the above catalyst.

$$M_a P_c D/S \tag{1}$$

Where,

M is a metal cluster or metal complex compound selected from the group of VIII, VII and VI elements;
S is an inorganic carrier such as $SiO_2$;
P is a promoter of phosphorus compound;
D is a cobalt compound such as $CoCl_2$;
"a" is weight percentage of metal cluster or metal complex compound in catalyst, having a value of 0.01 to 10; "c" is weight percentage of promoter in catalyst, ranging from 1.0 to 35.0.

BACKGROUND OF THE INVENTION

In general, ethylene has been widely used as one of the basic reaction chemicals in the field of petrochemical industry and fine chemical industry. It is well known that synthesis of ethylene from methane by dehydrogenation is conducted at relatively high temperature of about 1500° to 1550° C. through thermal or electric cracking reaction process.

However, this method causes some problems such as loss of an enormous amount of thermal energy and necessity of using high temperature equipment, and particularly severe corrosion of the reactor owing to high temperature.

As prior art describing synthesis of hydrocarbons by oxidative coupling and dehydrogenation in order to prepare lower hydrocarbons such as ethylene having a double bond by direct conversion of 5118654, Canadian Patent No. 2016675 and Japanese Patent Nos. 04352730, 04368342.

Above-referenced processes have more or less settled some disadvantages since the reaction is conducted at relatively lower temperature of about 700° to 800° C. However, since the reaction is conducted with oxygen, helium, nitrogen and $N_2O$ as oxidation or dilution gas, variety of reactants and a large amount of by-proudcts such as $CO_2$ are ensuing. Moreover, there are much difficulties in separating or purifying the reactants, let alone the inability to conduct a continuous process and the causation of a severe environmental pollution problem.

In the meantime, natural gas contains impurities such as carbon dioxide, $H_2S$ and moisture other than methane as the major ingredient. These impurities may affect catalytic activity, if they are not purified and the reaction cannot proceed properly.

SUMMARY OF THE INVENTION

In order to be free of said disadvantages associated with the above-referenced processes, it is therefore an object of the present invention to provide a method for preparation of high-yield ethylene with an available continuous process at relatively lower temperature in the presence of the catalyst, without generation of by-products such as carbon dioxide. Another object of the present invention is to provide a direct and continuous conversion method of methane containing some impurities, such as natural gas, to ethylene. A further object of the present invention is to provide a new catalyst used in said process and preparation thereof.

To fulfill said object, an intensive study has been made by the inventor and it is found that the conversion catalyst may be made available through the following process:

By the operation of converting methane or methane-containing gas directly in the presence of the catalyst expressed as said general formula (1) at a temperature of 350° to 1050° C., ethylene with high yield may be obtained without by-products such as carbon dioxide. Also, by the operation of adding solvent to the components of said general formula (1), suspended, agitated in reflux at a temperature of about 20° to 200° C., evaporated residues by distillation under reduced pressure and dried in a vacuum drier, said catalyst can be obtained.

In other words, the catalyst for conversion of the present invention is employed in converting methane or methane-containing gas into ethylene, and is characterized by expressing as general formula (1). The process for manufacturing the catalyst for conversion of the present invention is characterized by the following operation, wherein the components of said general formula (1) are added with solvent, suspended, agitated in reflux at a temperature of about 20° to 200° C., evaporated residues by distillation under reduced pressure and dried in vacuum drier. The process for manufacturing ethylene of the present invention is characterized by the direct conversion of methane or methane-containing gas into ethylene at a temperature of 350° to 1050° C. under 1 to 10 atm in the presence of said catalyst.

DETAILED DESCRIPTION OF THE INVENTION

The present invention will be described in more detail as follows:

The catalyst in the present invention is expressed by said general formula (1). In said formula (1), M is a metal cluster or metal complex compound such as Fe, Ru, Os, Co, Rh, Ir, Ni, Pd, Pt in VIII series, Mn, Re in VII series and Mo, W in VI series.

For example, the metal compound includes $RuCl_2(PPh_3)_3$, $RuCl_2(CO)_2(PPh_3)_2$, $Ru_3(CO)_{12}$, $RuCl(CO)(PPh_3)_2$, $IrCl(CO)(PPh_3)_2$, $Pd(PPh_3)_4$, $Pt(PPh_3)_4$, $RuCl_3.xH_2O$, $RhCl_3.H_2O$, $IrCl_3.xH_2O$, $H_2PtCl_6.xH_2O$, and $PdCl_2$. Among them, the most preferable metal compounds are the Ru and Rh series.

S is an inorganic carrier such as $\alpha$-$Al_2O_3$, $\gamma$-$Al_2O_3$, $SiO_2$, $SiO_2$—$Al_2O_3$, Y-zeolite, ZSM-5, zeolite, MgO, and $TiO_2$. Among them, the most preferable compounds are $\alpha$-$Al_2O_3$ and MgO. P is a promoter of phosphorous compound such as $PPh_3$, $P(OCH_3)_3$, $P(OC_2H_5)_3$, and $P(O)(OC_2H_5)_3$. D is cobalt compound such as $CoCl_2.xH_2O$, $Co(NO_3)_2.xH_2O$, and $Co(CH_3COO)_2.xH_2O$.

In a case where the methane contains some impurities, a cobalt compound is used to prevent the lowering of catalytic activity and also to prevent the reduction of yield even in the absence of dilution gas such as $N_2$. Its optimum use should be preferably in the range of below 0.3 wt %. If this range is exceeded, bonding interference among catalysts occurs and this may lead to reduction of catalytic activity.

And "a" is weight percentage of metal cluster or metal complex compound in catalyst, having a value of 0.01 to 10, "c" is weight percentage of promoter in catalyst, ranging from 1.0 to 35.0. If "a" exceeds the above value, it may be associated with reduction of yield and if "c" exceeds the above level, the inlet or outlet of reactor may be blocked.

The catalyst for conversion of the present invention is obtained by the following steps;

(i) Adding said M, P, D and S to solvent such as dichloromethane or acetone at a temperature of 20° to 200° C.

(ii) Mixing and suspending by refluxing.

(iii) Drying by distillation under reduced pressure.

Reaction conditions of direct converting of methane or methane-containing gas into ethylene in the presence of said catalyst according to the present invention are as follows:

Reaction temperature is 350° to 1050° C., preferably in the range of 650° to 950° C.

Reaction pressure is 1 to 10 atm, preferably in the range of 1 to 5 atm and more preferably normal pressure.

Concentration of catalyst is below 5.0 wt %, preferably 1.0 to 3.0 wt %.

Flow rate of source gas is 150 to 12000 cc/hr, preferably in the range of 600 to 4800 cc/hr.

Through the above process of the present invention, the rate of conversion of methane to ethylene is about 15 to 20%, which is lower than that of above-referenced processes to prepare ethylene based upon oxidative coupling and dehydrogenation reaction, showing 50 to 60%.

However, in the present invention, the productivity is improved further because the continuous conversion reaction can be effectively carried out without generating by-products such as carbon dioxide.

Even in the case when the methane for conversion contains some impurities, the catalytic activity may not be affected in the present invention. So there is great advantage to directly convert natural gas into ethylene without purifying.

Normally weight percentage of carbon dioxide in natural gas is 0 to 5% in average. In case of using the catalyst for conversion of the present invention, a stable methane conversion rate of 8.2 to 10.1% is attainable with the range of carbon dioxide content being 0.2 to 1.0%. And normally weight percentage of $H_2S$ in natural gas is below 1%. In case of using the catalyst of the present invention, about 14% of stable methane conversion rate is attainable, even if 1% of $H_2S$ is contained.

In addition to that, a small amount of water may be contained in natural gas. In case of using the catalyst of the present invention, 8 to 12% of stable conversion rate is attainable even if water is contained. In other words, if the catalyst of the present invention is used, a stable conversion rate is attainable of more than 10% regardless of the presence of any impurities. Also unconverted methane, passed through the reactor, can be used in the conversion reaction without purification.

EXAMPLES

The examples of the present invention are as follows and the definitions for conversion rate, yield and selectivity are defined below.

Conversion rate (mol %)=(mol Nos. of methane reacted/mol Nos. of methane supplied)×100

Yield (mol %)=(mol Nos. of lower hydrocarbon produced/mol Nos. of methane supplied)×100

Selectivity (mol %)=(mol Nos. of lower hydrocarbon produced/mol Nos. of methane reacted)×100

PREPARATION EXAMPLE 1

Preparation of Ru-series Catalyst 5.16 g of $\alpha$-$Al_2O_3$, 1.00 g (1.04 mmol) of $RuCl_2(PPh_3)_3$, 1.09 g (4.16 mmol) of $PPh_3$ and 0.01 g of $CoCl_2 \cdot xH_2O$ were added to mixed solvent consisting of 20 ml of dichloromethane and 10 ml of acetone, and stirred for about 30 minutes at a temperature of around 40° to 60° C.

This suspension obtained by above procedure was evaporated by distillation under reduced pressure, then dried in a vacuum drier for about 20 hours to prepare $RuCl_2(PPh_3)_3 \cdot PPh_3/\alpha$-$Al_2O_3$ (2 wt % Ru) catalyst.

PREPARATION EXAMPLE 2

Preparation of Ru-series Catalyst Containing Moisture 1.0 g of $RuCl_2(PPh_3)_3 \cdot PPh_3/\alpha$-$Al_2O_3$ (2 wt % Ru) catalyst, which was prepared in PREPARATION EXAMPLE 1, was dipped into 2 ml of distilled water for a few minutes and then, dried in a vacuum drier for 20 hours to prepare $RuCl_2(PPh_3)_3 \cdot PPh_3 \cdot H_2O/\alpha$-$Al_2O_3$ (2 wt % Ru) catalyst containing moisture.

PREPARATION EXAMPLE 3

Preparation of Ir-series Catalyst

This catalyst was prepared in the same manner as in PREPARATION EXAMPLE 1, except for substituting 0.78 g of $IrCl(CO)(PPh_3)_2$ for 1.00 g of $RuCl_2(PPh_3)_3$.

PREPARATION EXAMPLE 4

Preparation of Rh-series Catalyst

This catalyst was prepared in the same manner as in PREPARATION EXAMPLE 1, except for substituting 0.69 g of $RhCl(CO)(PPh_3)_2$ for 1.00 g of $RuCl_2(PPh_3)_3$.

PREPARATION EXAMPLE 5

Preparation of Pd-series Catalyst

This catalyst was prepared in the same manner as in PREPARATION EXAMPLE 1, except for substituting 1.16 g of $Pd(PPh_3)_4$ for 1.00 g of $RuCl_2(PPh_3)_3$.

PREPARATION EXAMPLE 6

Preparation of Pt-series Catalyst

This catalyst was prepared in the same manner as in PREPARATION EXAMPLE 1, except for substituting 1.24 g of $Pt(PPh_3)_4$ for 1.00 g of $RuCl_2(PPh_3)_3$.

EXAMPLE 1

Methane without dilution gas was introduced at 600 to 2400 cc/hr of flow rate into continuous stationary phase flow reactor (inner diameter: 0.70 cm, length: 40 cm, stuff: stainless steel 316) in the presence of the catalyst prepared in PREPARATION EXAMPLE 1.

Products obtained by continuous reaction under 1 atm at the temperature of 810° C. were analyzed by gas chromatography and the catalytic activity was as shown in the following Table 1.

TABLE 1

Comparison of catalytic activity according to flow rate

| Flow rate (cc/hr) | Conversion rate (%) | Yield (%) Ethylene | Yield (%) Ethane | Selectivity (%) Ethylene | Selectivity (%) Ethane |
|---|---|---|---|---|---|
| 600 | 17.1 | 15.5 | 1.6 | 90.6 | 9.4 |
| 900 | 15.9 | 14.5 | 1.4 | 91.2 | 8.8 |
| 1200 | 15.5 | 14.3 | 1.2 | 92.3 | 7.7 |
| 2400 | 14.1 | 12.8 | 1.3 | 90.8 | 9.2 |

EXAMPLE 2

In order to verify differences of using dilution gas and not using dilution gas, and effect of carbon dioxide contained as impurity in natural gas on catalytic activity, the reaction conducted in the same manner as in EXAMPLE 1 by supplying source gas mixing each of methane, nitrogen and carbon dioxide in the presence of the catalyst obtained in PREPARATION EXAMPLE 1. The results were as shown in following Table 2.

TABLE 2

Comparison of conversion rate in case of containing nitrogen and carbon dioxide

| Mixing ratio (cc/min) $CH_4:N_2:CO_2$ | Conversion rate (%) | Yield (%) Ethylene | Yield (%) Ethane | Selectivity (%) Ethylene | Selectivity (%) Ethane |
|---|---|---|---|---|---|
| 10:10:0 | 12.1 | 11.0 | 1.1 | 90.9 | 9.1 |
| 10:5:0 | 14.4 | 13.2 | 1.2 | 91.7 | 8.3 |
| 10:0:0 | 17.1 | 15.5 | 1.6 | 90.6 | 9.4 |
| 10:0:1 | 8.2 | 5.8 | 2.4 | 70.7 | 29.3 |
| 10:0:0.2 | 10.1 | 8.0 | 2.1 | 79.2 | 20.8 |

EXAMPLE 3

Effect of moisture contained in natural gas on catalytic activity was measured as shown in the following Table 3, at the result of the reaction conducted in the same manner as in EXAMPLE 1 in the presence of the catalyst obtained in PREPARATION EXAMPLE 2.

TABLE 3

Effect of moisture on catalytic activity

| Mixing ratio (cc/min) $CH_4:N_2$ | Reaction time (hr) | Conversion rate (%) | Yield (%) Ethylene | Yield (%) Ethane | Selectivity (%) Ethylene | Selectivity (%) Ethane |
|---|---|---|---|---|---|---|
| 10:10 | 3 | 6.9 | 6.3 | 0.6 | 91.3 | 8.7 |
| 10:10 | 14 | 11.2 | 10.3 | 0.9 | 92.0 | 8.0 |
| 10:0 | 3 | 11.6 | 9.4 | 2.2 | 81.0 | 19.0 |

EXAMPLE 4

In order to verify the effect of sulfur compound contained in natural gas on catalytic activity, the reaction conducted in the same manner as in EXAMPLE 1 in the presence of the catalyst obtained in PREPARATION EXAMPLE 1. The result was as shown in following Table 4.

TABLE 4

Effect of sulfur on catalytic activity

| Reaction time (hr) | Conversion rate (%) | Yield (%) Ethylene | Yield (%) Ethane | Selectivity (%) Ethylene | Selectivity (%) Ethane |
|---|---|---|---|---|---|
| 2 | 8.3 | 5.5 | 2.8 | 66.3 | 33.7 |
| 30 | 14.0 | 11.9 | 2.1 | 85.0 | 15.0 |

EXAMPLE 5

Effects of each catalyst obtained in PREPARATION EXAMPLE 3 to 7 on catalytic activity were measured as shown in the following Table 5, at the result of the reaction conducted in the same manner as in EXAMPLE 1 at a flow rate of 1200 cc/hr.

TABLE 5

Comparison of catalytic activity according to each catalyst

| Catalyst | Conversion rate (%) | Yield (%) Ethylene | Yield (%) Ethane | Selectivity (%) Ethylene | Selectivity (%) Ethane |
|---|---|---|---|---|---|
| PREPA. EXAMPLE 3 | 12.2 | 11.1 | 1.1 | 91.0 | 9.0 |
| PREPA. EXAMPLE 4 | 15.2 | 14.0 | 1.2 | 92.1 | 7.9 |
| PREPA. EXAMPLE 5 | 12.0 | 11.0 | 1.0 | 91.7 | 8.3 |
| PREPA. EXAMPLE 6 | 12.1 | 11.0 | 1.0 | 90.9 | 9.1 |

What is claimed is:

1. A catalyst for conversion of methane to ethylene comprises a compound of the general formula:

$$M_a P_c D/S \qquad (1)$$

wherein M is a metal cluster or metal complex compound containing a metal selected from metals of Groups VIII, VII and VI and comprising at least one member selected from the group consisting of $RuCl_2(PPh_3)_3$, $RuCl_2(CO)_2(PPh_3)_2$, $Ru_3(CO)_{12}$, $RuCl(CO)(PPh_3)_2$, $IrCl(CO)(PPh_3)_2$, $Pd(PPh_3)_4$, $Pt(PPh_3)_4$, $RuCl_3 \cdot xH_2O$, $RhCl_3 \cdot xH_2O$, $IrCl_3 \cdot xH_2O$, $H_2PtCl_6 \cdot xH_2O$, and $PdCl_2$;

S is an inorganic carrier;

P is a phosphorus compound promoter;

D is a cobalt compound;

wherein a is an amount of M corresponding to 0.01 to 10 wt. % of said catalyst and c is an amount of P corresponding to 1.0 to 35.0 wt. % of said catalyst.

2. A process for converting methane to ethylene comprising:

contacting a source gas comprising methane with a conversion catalyst, said catalyst comprising a compound of the general formula:

$$M_a P_c D/S \qquad (1)$$

wherein M is a metal cluster or metal complex compound containing a metal selected from the group consisting of Group VIII, VII and VI metals;

S is an inorganic carrier;

P is a phosphorus compound promoter;

D is a cobalt compound;

wherein a is an amount of M corresponding to 0.01 to 10 wt. % of said catalyst and c is an amount of P corresponding to 1.0 to 35.0 wt. % of said catalyst at a temperature of 350°–1050° C. under 1–10 atm. pressure;

catalytically converting the methane to ethylene; and recovering the ethylene so formed.

3. A catalyst for conversion as claimed in claim 1, wherein S comprises at least one member selected from the group consisting of $\alpha$-$Al_2O_3$, $\gamma$-$Al_2O_3$, $SiO_2$, $SiO_2Al_2O_3$, Y-zeolite, ZSM-5, zeolite, MgO, and $TiO_2$.

4. A catalyst for conversion as claimed in claim 1, wherein D comprises at least one member selected from the group consisting of $CoCl_2.xH_2O$, $Co(NO_3)_2.xH_2O$, and $Co(CH_3COO)_2.xH_2O$.

5. A catalyst for conversion as claimed in claim 1, wherein the weight percentage of D is below 0.3 wt %.

6. A process for preparing a catalyst for conversion as claimed in claim 1 comprising the following steps;

(i) adding M, P, D and S as defined in said general formula (1) to solvent at a temperature of 20° to 200° C.;

(ii) mixing and suspending by refluxing; and (iii) drying by distillation under reduced pressure.

7. A process for preparing ethylene as claimed in claim 2, wherein the velocity range of the source gas is 150 to 12000 cc/hr.

8. A process for preparing ethylene as claimed in claim 2, wherein the concentration of the catalyst for conversion is below 5 wt % of the source gas.

9. A process for preparing ethylene as claimed in claim 2, wherein the source gas is free of a dilution gas.

* * * * *